United States Patent [19]

Tanaka et al.

[11] 4,293,695
[45] Oct. 6, 1981

[54] FURONAPHTHYRIDINE COMPOUNDS

[75] Inventors: Yoshiaki Tanaka; Isao Hayakawa, both of Minamifunabori, Japan

[73] Assignee: Daiichi Seiyaku Co., Ltd., Tokyo, Japan

[21] Appl. No.: 191,620

[22] Filed: Sep. 29, 1980

Related U.S. Application Data

[63] Continuation of Ser. No. 8,205, Jan. 31, 1979, abandoned.

[30] Foreign Application Priority Data

Jun. 9, 1978 [JP] Japan ................................. 53-69685

[51] Int. Cl.³ .................................... C07D 491/147
[52] U.S. Cl. ..................................... 546/83; 424/256; 546/123; 546/297
[58] Field of Search ............................ 546/83

[56] References Cited

U.S. PATENT DOCUMENTS 3,663,559  5/1972  Derijckere et al. .............. 546/83 X
4,079,058  3/1978  Ackermann et al. ............. 546/83 X

OTHER PUBLICATIONS

*Chemical Abstracts*, 88: 152461f, (1978), [Heindl, J., et al., *Eur. J. Med. Chem.-Chim. Ther.*, 1977, 12(6), 549–555].

*Chemical Abstracts*, 76: 72499m, (1972), [Albrecht, R., et al., German Ols. No. 2,030,899, 12/23/71].

*Primary Examiner*—Richard A. Schwartz
*Attorney, Agent, or Firm*—Sughrue, Mion, Zinn, Macpeak & Seas

[57] ABSTRACT

2,3,5,8-Tetrahydrofuro- and 5,8-dihydrofuro[3,2-b]-1,8-naphthyridine compounds of the formula (I)

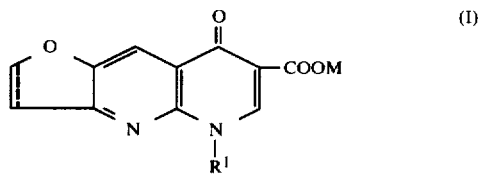

wherein $R^1$ represents an alkyl group having 1 to 6 carbon atoms and M represents a hydrogen atom, an alkali metal or an alkaline earth metal having anti-bacterial activity.

6 Claims, No Drawings

FURONAPHTHYRIDINE COMPOUNDS

This is a continuation of application Ser. No. 8,205, filed Jan. 31, 1979, now abandoned.

BACKGROUND OF THE INVENTION

1. Field of the Invention

This invention relates to a novel anti-bacterial agent and, more particularly, this invention relates to 2,3,5,8-tetrahydrofuro- and 5,8-dihydrofuro[3,2−b]-1,8-naphthyridine compounds of the formula (I)

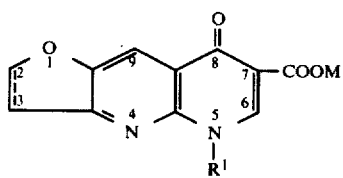

wherein $R^1$ represents an alkyl group having 1 to 6 carbon atoms and M represents a hydrogen atom, an alkali metal or an alkaline earth metal, having excellent anti-bacterial activity against both the gram-negative and gram-positive bacteria.

2. Description of the Prior Art

The compound of this invention has excellent anti-bacterial activity against gram-negative and gram-positive bacteria and its activity is superior to oxolinic acid (5-ethyl-5,8-dihydro-8-oxo-1,3-dioxolo[4,5-g]quinoline-7-carboxylic acid) which has a chemical structure similar to the compound of this invention and which is known as an excellent anti-bacterial agent described in Japanese Patent Publication No. 5666/1967 and *J. Med. Chem.*, 11 160 (1968). Also, its activity is believed stronger than that of 5-ethyl-2,3,5,8-tetrahydro-8-oxofuro[2,3−g]quinoline-7-carboxylic acid which is known to have anti-bacterial activity equivalent to oxolinic acid as described in *Chemical Abstracts*, 76, p. 72499, U.S. Pat. No. 3,773,769, German Pat. (OLS) No. 2,030,899, Japanese patent application (OPI) No. 1081/1972.

SUMMARY OF THE INVENTION

A principal object of the present invention is to provide a novel anti-bacterial agent having very low toxicity.

A further object of this invention is to provide an anti-bacterial agent which is effective against both gram-negative and gram-positive bacteria, and particularly against *Pseudomonas aeruginosa*.

A still further object of this invention is to provide an anti-bacterial agent which has a stronger anti-bacterial effect than known agents such as 5-ethyl-2,3,5,8-tetrahydro-8-oxofuro[2,3−g]quinoline-7-carboxylic acid and oxolinic acid.

These and other objects of the present invention are accomplished by a compound of the formula (I) which is described below in detail.

DETAILED DESCRIPTION OF THE INVENTION

In the formula (I), the dotted line used in the furan ring moiety, i.e.,

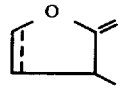

represents a single bond or two hydrogen atoms and, therefore, the compounds of this invention having the formula (I) include 5,8-dihydrofuro[3,2−b]-1,8-naphthyridines of the formula (Ia) and 2,3,5,8-tetrahydrofuro[3,2−b]-1,8-naphthyridines of the formula (Ib)

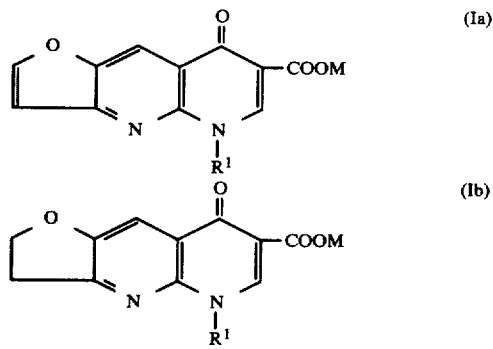

wherein $R^1$ and M are as defined above.

In the present invention, the compounds of the formula (Ia) are preferred to those of the formula (Ib) from the standpoint of anti-bacterial activity.

The compounds of this invention can be prepared by the following reaction scheme:

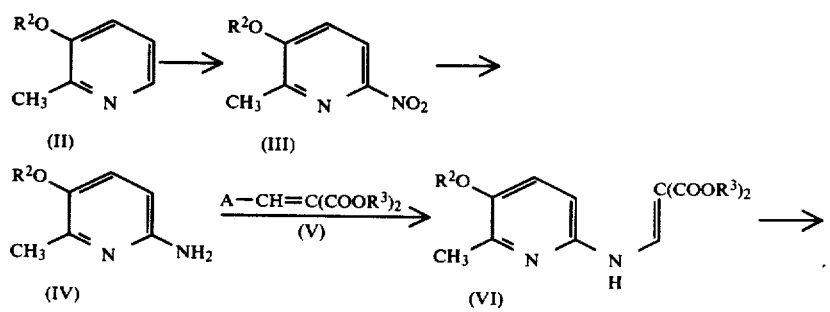

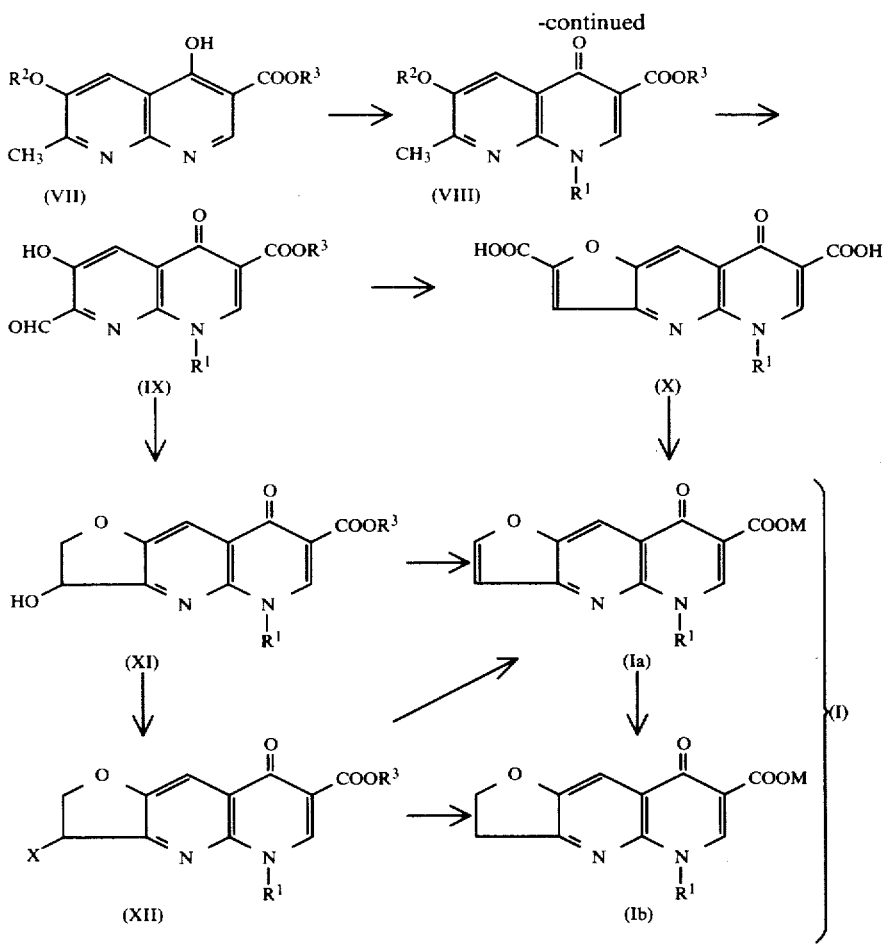

wherein $R^1$, $R^2$ and $R^3$ each represents a straight or branched chain alkyl group having 1 to 6 carbon atoms, for example, a methyl, ethyl, n-propyl, isopropyl or n-butyl group, X represents a halogen atom, for example, a chlorine, bromine or iodine atom, A represents an alkoxy group having 1 to 6 carbon atoms such as an ethoxy group or a dialkylamino group wherein each of the alkyl moieties thereof has 1 to 6 carbon atoms, for example, a dimethylamino or diethylamino group, and M represents a hydrogen atom, or an alkali or alkaline earth metal atom, for example, a sodium, potassium, calcium or magnesium atom, preferably a sodium atom.

In the above processes, a 3-alkoxy-2-methylpyridine of the formula (II) is first nitrated to yield a 3-alkoxy-2-methyl-6-nitropyridine of the formula (III) which is then reduced to a 3-alkoxy-2-methyl-6-aminopyridine of the formula (IV). The nitration can be effected in a usual manner, for example, using fuming nitric acid in the presence of sulfuric acid at a temperature of about 0° C. to about 40° C., preferably at room temperature (about 15° to 30° C.) with stirring, and the reduction can be carried out using a catalyst such as palladium black, Raney nickel and the like in a solvent, for example, an alcohol such as methanol, ethanol and the like.

The resulting compound of the formula (IV) and an alkoxymethylenemalonic acid ester or a dialkylaminomethylenemalonic acid ester compound of the formula (V) are then heated at about 50° to about 150° C. in the presence or absence of an organic solvent, for example, an alcohol such as methanol, ethanol and the like or chloroform, preferably in the presence of an alcohol, to yield a 3-alkoxy-2-methyl-6-(2,2-dialkoxycarbonylethenyl)aminopyridine of the formula (VI) which is then heated at about 200° to about 260° C. in a non-polar solvent having a high boiling point between about 200° C. and about 300° C. such as diphenyl ether, biphenyl and the like to yield a 6-alkoxy-7-methyl-4-hydroxy-1,8-naphthyridine-3-carboxylic acid ester of the formula (VII).

The resulting compound of the formula (VII) is alkylated in a common manner such as by heating the compound of the formula (VII) and an alkyl halide, for example, ethyl iodide in the presence of a hydrogen halide acceptor such as potassium carbonate, sodium carbonate, a tertiary amine, e.g., triethylamine, or by alkylating with a dialkylsulfuric acid to yield a 1,4-dihydro-1-alkyl-4-oxo-6-alkoxy-7-methyl-1,8-naphthyridine-3-carboxylic acid ester of the formula (VIII), which is converted to a 1,4-dihydro-1-alkyl-4-oxo-6-hydroxy-7-formyl-1,8-naphthyridine-3-carboxylic acid ester (IX) by a combination of two reactions, i.e., oxidation and hydrolysis in this order or in a reverse order, preferably in the order of first oxidation and then hydrolysis.

Oxidation of the 7-methyl group by an oxidizing agent such as selenium dioxide and the like yields a formyl group at the 7-position, and hydrolysis of the 6-alkoxy group by a Lewis acid such as aluminum halide, boron bromide and the like yields a hydroxyl group at the 6-position. The oxidation can be carried out by heating the compound of the formula (VIII) in the presence or absence of a solvent, preferably in the presence of a solvent such as sulfolane, dimethyl sulfone and the like. The hydrolysis can be effected in dichloromethane or carbon disulfide, preferably in dichloromethane at room temperature.

The compound of the formula (IX) is then subjected to a conventional ring closure reaction, for example, the Weis' reaction as described in *J. Heterocyclic Chem.*, 15 29 (1978) by heating the compound in the presence of a bromomalonic acid ester in a solvent such as dimethylformamide, methyl ethyl ketone, dichloroethane and the like, preferably dichloroethane, in the presence of a hydrogen halide acceptor such as triethylamine, potassium carbonate and the like and treating with an acid, for example, diluted sulfuric acid and the like, or an alkali, for example, potassium carbonate, sodium hydroxide and the like, preferably diluted sulfuric acid, most preferably 20 V/V% aqueous sulfuric acid to yield a 5,8-dihydro-5-alkyl-8-oxofuro[3,2−b]-1,8-naphthyridine-2,7-dicarboxylic acid of the formula (X) via hydrolysis, decarboxylation and dehydration of the intermediate,

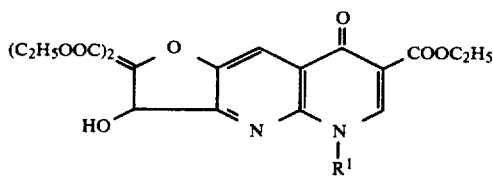

The resulting compound of the formula (X) is then decarboxylated by heating the compound while refluxing in a solvent such as dimethylacetamide, dimethylformamide or quinoline in the presence of copper powder, cuprous oxide or cupric oxide, preferably in dimethylacetamide in the presence of cuprous oxide to yield a 5,8-dihydro-5-alkyl-8-oxofuro[3,2-b]-1,8-naphthyridine-7-carboxylic acid of the formula (Ia).

The compound (IX) can also be treated with trimethylsulfoxonium iodide [((CH$_3$)$_3$S=O)+I$^-$] according to Holt's method as described in *Tetrahedron Lett.*, 683 (1966), for example, in dimethyl sulfoxide at room temperature while stirring in a nitrogen atmosphere, to yield a 5-alkyl-3-hydroxy-8-oxo-2,3,5,8-tetrahydrofuro[3,2-b]-1,8-naphthyridine-7-carboxylic acid ester of the formula (XI) which is then heated to dehydrate the furan ring and hydrolyze the ester moiety, preferably using an acid, to yield the compound (Ia).

When the compound (XI) is converted to a 3-halogen compound (XII) by treatment with a halogenating agent, for example, a thionyl halide such as thionyl chloride in a non-polar solvent, for example, chloroform, and the compound (XII) is catalytically reduced in the presence of a palladium black or Raney nickel and hydrolyzed by heating in the presence of an acid such as hydrochloric acid, sulfuric acid and the like or an alkali such as sodium hydroxide, or when the compound (Ia) is catalytically reduced in the same manner as described above, 2,3,5,8-tetrahydro compound, i.e., 5-alkyl-8-oxo-2,3,5,8-tetrahydrofuro[3,2−b]-1,8-naphthyridine-7-carboxylic acid of the formula (Ib) can be prepared.

When the 3-halogen compound (XII) is dehydrohalogenated with a base in the presence of a hydrogen halide acceptor such as 1,8-diazabicyclo[5,4,0]-7-undecene or triethylamine and hydrolyzed by heating in the presence of an acid such as hydrochloric acid, sulfuric acid and the like, the compound (Ia) can be prepared. The compound (Ia) and compound (Ib) can be changed to the alkali metal salt or alkaline earth metal salt thereof in the usual manner.

The compound of this invention has an excellent anti-bacterial activity, whereas it exhibits very low toxicity. Thus, these compounds are very useful anti-bacterial agents. The anti-bacterial activity (in vitro) and the acute toxicity (LD$_{50}$) of the compounds of this invention are shown in the following Table in comparison with known oxolinic acid.

TABLE

| Minimum Inhibitory Concentration (MIC, μg/ml)* | | | |
|---|---|---|---|
| Test Organisms | Compound Ia R$^1$ = C$_2$H$_5$ | Compound Ib R$^1$ = C$_2$H$_5$ | Oxolinic Acid |
| *E. coli* NIHJ | ≦ 0.2 | ≦ 0.2 | ≦ 0.2 |
| *Pr. mirabilis* | ≦ 0.2 | ≦ 0.2 | |
| *Pr. vulgaris* | ≦ 0.2 | ≦ 0.2 | |
| *K. pneumoniae*, Type 1 | 1.6 | 0.8 | 3.1 |
| *Ser. marcescens* 13014 | 0.4 | ≦ 0.2 | 0.8 |
| *Ent. cloacae* 12001 | 0.4 | ≦ 0.2 | 0.8 |
| *Ps. aeruginosa* 2063 | 3.1 | 6.3 | 25 |
| *S. aureus* | 3.1 | 3.1 | 3.1 |
| LD$_{50}$ (mice i.v. mg/kg) | 221.3 | 375.8 | |

*Determined by the standard method of Japan Society of Chemotherapy: dilution method on plate culture (heart infusion agar culture), 10$^6$/ml of bacteria were seeded and incubated at 37° C. for 18 hours.

The present invention is further illustrated by the following Examples. Unless otherwise indicated, all parts, percents, ratios and the like are by weight.

EXAMPLE 1

To a solution of 70 g of 3-ethoxy-2-methylpyridine (Compound II where R$^2$=C$_2$H$_5$) dissolved in 280 ml of sulfuric acid under ice-cooling, a mixed solution of 42 ml of fuming nitric acid and 50 ml of concentrated sulfuric acid was added dropwise while stirring and keeping the internal temperature at 0° to 3° C. After stirring for additional 30 minutes at the same temperature, the reaction mixture was poured into ice water and extracted with chloroform. The extract was washed with water, dried over anhydrous sodium sulfate and concentrated to give 85 g of 3-ethoxy-2-methyl-6-nitropyridine (Compound III where R$^2$=C$_2$H$_5$), m.p. 90°-92° C.

| Elemental Analysis | | | |
|---|---|---|---|
| | C | H | N |
| Calcd. for C$_8$H$_{10}$N$_2$O$_3$: | 52.74 | 5.53 | 15.38 |
| Found: | 52.53 | 5.47 | 15.21 |

18.2 g of the nitro compound obtained above was suspended in 300 ml of ethanol, which was reduced over 2 g of 5% palladium black under atmospheric pressure. After reaction, the catalyst was filtered off and the solvent was evaporated in vacuo. The residue was crystallized from benzene to obtain 13.8 g of 3-ethoxy-2-methyl-6-aminopyridine (Compound IV where R$^2$=C$_2$H$_5$), m.p. 98°-99° C.

| Elemental Analysis | | | |
|---|---|---|---|
| | C | H | N |
| Calcd. for C$_8$H$_{12}$N$_2$O: | 63.13 | 7.95 | 18.41 |
| Found: | 63.38 | 8.04 | 18.27 |

A solution of 10.6 g of the amino compound obtained as above and 15.9 g of diethyl ethoxymethylenemalonate (Compound V where $A=C_2H_5O$ and $R^3=C_2H_5$) dissolved in 30 ml of ethanol was refluxed for 1 hour and allowed to cool. The crystals were precipitated by adding isopropyl ether and collected by filtration to obtain 19.0 g of 3-ethoxy-2-methyl-6-(2,2-diethoxycarbonylethenyl)aminopyridine (Compound VI where $R^2=R^3=C_2H_5$) which when recrystallized from ethanol had a melting point of 137°–138° C.

Elemental Analysis

|  | C | H | N |
|---|---|---|---|
| Calcd. for $C_{16}H_{22}N_2O_5$: | 59.61 | 6.88 | 8.69 |
| Found: | 59.92 | 6.71 | 8.63 |

16.1 g of the Compound VI obtained as above was added to 160 ml of boiling Dowtherm (produced by Dow Chemical Co.) and refluxed for 1 hour. After cooling, the precipitated crystals were collected by filtration to obtain 11.8 g of crude crystals which were then recrystallized from dimethylformamide to yield ethyl 6-ethoxy-4-hydroxy-7-methyl-1,8-naphthyridine-3-carboxylate (Compound VII where $R^2=R^3=C_2H_5$), m.p. 279°–282° C. (with decomposition).

Elemental Analysis

|  | C | H | N |
|---|---|---|---|
| Calcd. for $C_{14}H_{16}N_2O_4$: | 60.86 | 5.84 | 10.14 |
| Found: | 60.67 | 5.98 | 9.97 |

A mixture of 11.0 g of the Compound VII obtained above and 6.6 g of potassium carbonate in 110 ml of dimethylformamide was heated at 90°–100° C. for 10 minutes and 7.5 g of ethyl iodide was then added dropwise thereto.

The resulting mixture was stirred for an additional 1 hour at the same temperature. After filtering off the insoluble materials, the filtrate was concentrated under reduced pressure. To the residue obtained, water and chloroform were added. The chloroform layer separated out was washed with water, dried over anhydrous sodium sulfate and then concentrated to obtain 10.5 g of the crude crystals. Recrystallization from ethanol yielded ethyl 1,4-dihydro-6-ethoxy-1-ethyl-7-methyl-4-oxo-1,8-naphthyridine-3-carboxylate (Compound VIII where $R^1=R^2=R^3=C_2H_5$), m.p. 163°–164° C.

Elemental Analysis

|  | C | H | N |
|---|---|---|---|
| Calcd. for $C_{16}H_{20}N_2O_4$: | 63.14 | 6.62 | 9.21 |
| Found: | 62.93 | 6.59 | 9.36 |

20.2 g of the Compound VIII obtained as above was heated at 175°–185° C. under a nitrogen stream to melt and 10 g of selenium dioxide was added in several portions. Under a nitrogen stream, the mixture was reacted under the same conditions for 20 minutes. After allowing to cool, chloroform was added to the reaction mixture and the insoluble materials were removed by filtration and the filtrate was concentrated in vacuo. The resulting residue was recrystallized from ethanol to yield 13.2 g of ethyl 1,4-dihydro-6-ethoxy-1-ethyl-7-formyl-4-oxo-1,8-naphthyridine-3-carboxylate having a melting point of 169°–170° C.

Elemental Analysis

|  | C | H | N |
|---|---|---|---|
| Calcd. for $C_{16}H_{18}N_2O_5$: | 60.37 | 5.70 | 8.80 |
| Found: | 60.58 | 5.44 | 8.91 |

To a solution of 20.5 g of aluminum bromide in 450 ml of carbon disulfide, 3.95 g of the compound obtained above was added under ice-cooling, and the mixture was then refluxed for 1 hour. To the reaction solution, 500 ml of water was added and stirred. Chloroform was added to the solution for extraction. The chloroform layer which was separated out was washed with water, dried over anhydrous sodium sulfate and the solvent was evaporated in vacuo. The residue obtained was recrystallized from ethanol to yield 3.13 g of ethyl 1,4-dihydro-1-ethyl-7-formyl-6-hydroxy-4-oxo-1,8-naphthyridine-3-carboxylate (Compound IX where $R^1=R^3=C_2H_5$) having a melting point of 243°–245° C.

Elemental Analysis

|  | C | H | N |
|---|---|---|---|
| Calcd. for $C_{14}H_{14}N_2O_5$: | 57.93 | 4.86 | 9.65 |
| Found: | 58.04 | 4.82 | 9.57 |

To 300 ml of methyl ethyl ketone, 6.0 g of the above compound, 5.6 g of diethyl bromomalonate and 4.5 g of potassium carbonate were added and the mixture was refluxed for 9 hours. The resulting insoluble materials were filtered off and the filtrate was concentrated under reduced pressure.

The residue was purified by column chromatography on silica gel. Elution with chloroform followed by removal of the solvent yielded 6.1 g of triethyl 5-ethyl-3-hydroxy-8-oxo-2,3 5,8-tetrahydrofuro[3,2−b]-1,8-naphthyridine-2,2,7-tricarboxylate having a melting point of 193° C.

Elemental Analysis

|  | C | H | N |
|---|---|---|---|
| Calcd. for $C_{21}H_{24}N_2O_9$: | 56.24 | 5.39 | 6.25 |
| Found: | 55.80 | 5.32 | 6.21 |

1.2 g of the above compound and 0.48 g of potassium carbonate were added to a mixed solution of water (4 ml) and ethanol (14 ml). The solution was refluxed for 30 minutes and 5 ml of 2 N aqueous sodium hydroxide solution was then added thereto, and the mixture was reacted for an additional 30 minutes.

The reaction mixture was acidified with hydrochloric acid and the precipitated crystals were collected by filtration. The crude product was recrystallized from dimethylformamide to yield 0.52 g of 5,8-dihydro-5-ethyl-8-oxofuro[3,2−b]-1,8-naphthyridine-2,7-dicarboxylic acid (Compound X where $R^1=C_2H_5$), m.p. >300° C.

Elemental Analysis

|  | C | H | N |
|---|---|---|---|
| Calcd. for $C_{14}H_{10}N_2O_6$: | 55.63 | 3.34 | 9.27 |
| Found: | 55.91 | 3.42 | 9.35 |

A mixture of 525 mg of copper powder and 20 ml of quinoline was heated to 160° C., and 1.9 g of Compound X was added thereto under a stream of nitrogen. The internal temperature of the resulting mixture was allowed to rise to 195° C. and vigorous stirring was continued for an additional 15 minutes at the same temperature.

After cooling, the reaction mixture was added to 200 ml of chloroform and filtered to remove insoluble materials and the filtrate was then washed with 5% hydrochloric acid several times to remove the quinoline. Furthermore, the chloroform layer was washed with water, dried over anhydrous sodium sulfate and the solvent was evaporated in vacuo.

The resulting residue was subjected to column chromatography on silica gel. Elution with a mixture of chloroform and methanol (97:3) followed by removal of the solvent yielded a crude crystal. The crude product was recrystallized from dimethylformamide to obtain 1.1 g of 5,8-dihydro-5-ethyl-8-oxofuro[3,2-b]-1,8-naphthyridine-7-carboxylic acid (Compound Ia where $R^1=C_2H_5$), m.p. >260° C.

| Elemental Analysis | | | |
|---|---|---|---|
| | C | H | N |
| Calcd. for $C_{13}H_{10}N_2O_4$: | 60.46 | 4.26 | 10.88 |
| Found: | 60.79 | 3.90 | 10.85 |

EXAMPLE 2

To a mixture of 342 mg of 50% sodium hydride and 12 mg of anhydrous dimethyl sulfoxide, 1.59 g of trimethylsulfoxonium iodide was added with stirring under a stream of nitrogen at room temperature.

After stirring for 30 minutes, a solution of 1.74 g of ethyl 1,4-dihydro-1-ethyl-7-formyl-6-hydroxy-4-oxo-1,8-naphthyridine-3-carboxylate (Compound IX where $R^1=R^3=C_2H_5$) dissolved in 20 ml of anhydrous dimethyl sulfoxide was added dropwise to the mixture and stirred for 1 hour at room temperature.

The reaction mixture was poured into ice water and extracted with chloroform. The extract was washed with water, dried over anhydrous sodium sulfate and the solvent was evaporated in vacuo to obtain 1.2 g of ethyl 5-ethyl-3-hydroxy-8-oxo-2,3,5,8-tetrahydrofuro[3,2-b]-1,8-naphthyridine-7-carboxylate (Compound XI where $R^1=R^3=C_2H_5$).

When 35 mg of the compound obtained above in 2 ml of dimethyl sulfoxide was heated at 180°-190° C. for 20 hours, dehydration was accomplished to yield ethyl 5,8-dihydro-5-ethyl-8-oxofuro[3,2-b]-1,8-naphthyridine-7-carboxylate. The compound obtained as above was heated in 10% aqueous sodium hydroxide solution to obtain the corresponding carboxylic acid (Compound Ia where $R^1=C_2H_5$).

EXAMPLE 3

To a solution of 280 mg of the ethyl 5-ethyl-3-hydroxy-8-oxo-2,3,5,8-tetrahydrofuro[3,2-b]-1,8-naphthyridine-7-carboxylate (Compound XI where $R^1=R^3=C_2H_5$) obtained as in Example 2 dissolved in 5 ml of anhydrous chloroform, 100 mg of thionyl chloride was added dropwise at below 10° C. After stirring for 40 minutes, the reaction mixture was poured into ice water and neutralized with sodium bicarbonate. The chloroform layer then separated out, and was dried over anhydrous sodium sulfate and the solution was evaporated in vacuo.

300 mg of the crude ethyl 3-chloro-5-ethyl-8-oxo-2,3,5,8-tetrahydrofuro[3,2-b]-1,8-naphthyridine-7-carboxylate (Compound XII where $R^1=R^3=C_2H_5$) obtained above was dissolved in 30 ml of methanol, which was reduced over 5% palladium black (200 mg) under atmospheric pressure. After reaction, the catalyst was filtered off and the solvent was distilled off under reduced pressure to obtain 240 mg of crude ethyl 5-ethyl-8-oxo-2,3,5,8-tetrahydrofuro[3,2-b]-1,8-naphthyridine-7-carboxylate.

The product obtained was added to 5 ml of 10% aqueous sodium hydroxide solution and the mixture was heated to 100° C. for 1 hour. After cooling, the solution was acidified with hydrochloric acid and the crystals precipitated were collected by filtration, recrystallized from chloroformethanol to yield 5-ethyl-8-oxo-2,3,5,8-tetrahydrofuro[3,2-b]-1,8-naphthyridine-7-carboxylic acid (Compound Ib where $R^1=C_2H_5$), m.p. 292° C.

| Elemental Analysis | | | |
|---|---|---|---|
| | C | H | N |
| Calcd. for $C_{13}H_{12}N_2O_4$: | 59.99 | 4.65 | 10.77 |
| Found: | 59.77 | 4.72 | 10.59 |

EXAMPLE 4

100 mg of the 5,8-dihydro-5-ethyl-8-oxofuro[3,2-b]-1,8-naphthyridine-7-carboxylic acid (Compound Ia where $R^1=C_2H_5$) described as above was dissolved in 50 ml of methanol and reduced over 5% palladium black (100 mg) in a stream of hydrogen at an initial pressure of 4 atms.

By the treatment described above, 5-ethyl-8-oxo-2,3,5,8-tetrahydrofuro[3,2-b]-1,8-naphthyridine-7-carboxylic acid (Compound Ib where $R^1=C_2H_5$) as obtained in Example 3 was obtained.

EXAMPLE 5

A mixture of 30.4 g of ethyl 1,4-dihydro-6-ethoxy-1-ethyl-7-methyl-4-oxo-1,8-naphthyridine-3-carboxylate (Compound VIII where $R^1=R^2=R^3=C_2H_5$) and 100 ml of sulfolane was stirred at 140°-145° C. and 22 g of selenium dioxide in limited amounts was added thereto. After reacting the mixture under the same conditions for 5 hours and then allowing it to cool, chloroform was added thereto. The insoluble materials were removed by filtration. The filtrate was washed successively with 3% sodium carbonate solution, water, dried over anhydrous sodium sulfate and evaporated. To the residue was added isopropanol and the precipitated crystals were collected by filtration to obtain 22.0 g of ethyl 1,4-dihydro-6-ethoxy-1-ethyl-7-formyl-4-oxo-1,8-naphthyridine-3-carboxylate, m.p. 169°-170° C.

To 500 ml of dichloromethane was added 53 g of pulverized aluminium chloride and stirred at room temperature for 1 hour. To the above mixture, a solution of 25.0 g of ethyl 1,4-dihydro-6-ethoxy-1-ethyl-7-formyl-4-oxo-1,8-naphthyridine-3-carboxylate dissolved in 200 ml of dichloromethane was slowly added dropwise. After the resulting mixture was stirred at room temperature for 3 hours, ice water was added to the reaction mixture and allowed to separate into two layers. The aqueous layer was extracted with chloroform and the chloroform extract and the organic layer were combined, and washed with water, dried and evaporated in vacuo to obtain 21.8 g of ethyl 1,4-dihydro-1-ethyl-7-formyl-6-hydroxy-4-oxo-1,8-naphthyridine-3-carboxylate (Compound IX where $R^1 = R^3 = C_2H_5$), m.p. 243°–245° C.

EXAMPLE 6

To a solution of 3.2 g of ethyl 3-chloro-5-ethyl-8-oxo-2,3,5,8-tetrahydrofuro[3,2−b]-1,8-naphthyridine-7-carboxylate (Compound XII where $R^1 = R^3 = C_2H_5$, X=Cl) dissolved in 50 ml of dimethylformamide, 3.2 g of 1,8-diazabicyclo[5,4,0]-7-undecene was slowly added dropwise and the mixture was stirred at 40° to 45° C. for 1 hour. After removal of the solvent, the residue was dissolved in dilute hydrochloric acid and extracted with chloroform. The chloroform layer separated out was washed with water, dried and evaporated in vacuo to obtain 2.3 g of ethyl 5,8-dihydro-5-ethyl-8-oxofuro[3,2−b]-1,8-naphthyridine-7-carboxylate.

Elemental Analysis

|  | C | H | N |
|---|---|---|---|
| Calcd. for $C_{15}H_{14}N_2O_4$: | 62.93 | 4.93 | 9.79 |
| Found: | 62.75 | 5.06 | 9.67 |

To 30 ml of a solution of 1 N hydrochloric acid containing acetic acid at the concentration of 90%, 2.86 g of the compound obtained as above was added and refluxed for 2 hours. After cooling, the precipitated crystals were collected by filtration to obtain 1.85 g of 5,8-dihydro-5-ethyl-8-oxofuro[3,2−b]-1,8-naphthyridine-7-carboxylic acid (Compound Ia where $R^1 = C_2H_5$), m.p. 305°–307° C. (with decomposition).

NMR Spectrum ($CF_3COOH$): γ(ppm)

1.85 (3H, t, $CH_2\underline{CH_3}$)
5.30 (1H, q, $\underline{CH_2}CH_3$)
7.45 (1H, d-d, $C_3$—H)
8.65 (1H, d, $C_2$—H)
9.15 (1H, d, $C_8$—H)
9.70 (1H, s, $C_6$—H)

IR Spectrum (KBr): $cm^{-1}$ (in order of absorption intensity)

1715, 1480, 1390, 1600, 1420, 1620, 1440, 800, 1350, 1270.

To a suspension of 25.8 g of the compound obtained above in 250 ml of water, about 100 ml of 1 N aqueous sodium hydroxide solution was slowly added dropwise while stirring vigorously. The mixture was filtered to remove some of the insoluble materials. By gradually adding ethanol to the filtrate, the sodium salts were precipitated. After ice-cooling, the precipitated crystals were collected by filtration to yield 26.7 g of sodium 5,8-dihydro-5-ethyl-8-oxofuro-[3,2−b]-1,8-naphthyridine-7-carboxylate monohydrate, m.p. >300° C.

Elemental Analysis

|  | C | H | N |
|---|---|---|---|
| Calcd. for $C_{13}H_9N_2O_4Na \cdot H_2O$: | 52.33 | 3.72 | 9.40 |
| Found: | 52.18 | 3.84 | 9.27 |

5.0 g of triethyl 5-ethyl-3-hydroxy-8-oxo-2,3,5,8-tetrahydrofuro[3,2−b]-1,8-naphthyridine-2,2,7-tricarboxylate was added to 80 ml of 20% sulfuric acid and stirred at 100° C. for 2 hours. After allowing it to cool, the reaction solution was poured into ice water. The precipitated crystals were collected by filtration and recrystallized from dimethylformamide to obtain 2.61 g of 5,8-dihydro-5-ethyl-8-oxofuro-[3,2−b]-1,8-naphthyridine-2,7-dicarboxylic acid (Compound X where $R^1 = C_2H_5$), m.p. >300° C.

A mixture of 10.0 g of the compound obtained above, 120 mg of cuprous oxide in 300 ml of dimethylacetamide was refluxed for 3 hours and the hot reaction mixture was filtered to remove the insoluble material. The filtrate was concentrated and the precipitated crystals were collected by filtration. The crude crystals were dissolved in acetic acid, treated with charcoal and filtered. The filtrate was concentrated until a crystal precipitated and then allowed to cool. The precipitated crystals were collected by filtration, washed with ether and dried to obtain 5.7 g of 5,8-dihydro-5-ethyl-8-oxofuro[3,2−b]-1,8-naphthyridine-7-carboxylic acid (Compound Ia where $R^1 = C_2H_5$).

EXAMPLE 8

A mixture of 270 g of 5,8-dihydro-5-ethyl-8-oxofuro-[3,2−b]-1,8-naphthyridine-2,7-dicarboxylic acid (Compound X where $R^1 = C_2H_5$) and 3.24 g of cuprous oxide in 4 l of dimethylacetamide was heated under reflux for 2.5 hours. The reaction mixture was concentrated to dryness and the residue was washed with chloroform to obtain 203 g of the first crop. The chloroform solution was concentrated to dryness to give 12 g of the second crop.

The crude products obtained as above were combined and pulverized. The powder was heated under reflux with chloroform to dissolve. After removing the impurities by filtration, the filtrate was treated with 21.5 g of activated charcoal to decolorize. The resulting chloroform solution was poured on a silica gel column (500 g) and the product was eluted with 20 l of chloroform. The eluate was concentrated in vacuo to a volume of about 900 ml. The crystals precipitated were collected by filtration, washed with 800 ml of chloroform and dried to yield 126.4 g of 5,8-dihydro-5-ethyl-8-oxofuro[3,2−b]-1,8-naphthyridine-7-carboxylic acid (Compound Ia where $R^1 = C_2H_5$).

EXAMPLE 9

A mixture of 9.5 g of 5,8-dihydro-5-ethyl-8-oxofuro-[3,2−b]-1,8-naphthyridine-2,7-dicarboxylic acid (Compound X where $R^1 = C_2H_5$), 0.8 g of copper powder and 250 ml of diethyl phthalate was heated at 250° to 260° C. for 25 minutes. After cooling, the reaction mixture was separated by partitioning between chloroform and aqueous potassium carbonate solution. The aqueous layer which separated out was acidified with hydrochloric acid and extracted with chloroform. The extract was treated with charcoal, and washed with water, dried and concentrated. The crystals precipitated by adding ethanol were collected by filtration to obtain 4.2 g of 5,8-dihydro-5-ethyl-8-oxofuro[3,2−b]-1,8-naphthyridine-7-carboxylic acid (Compound Ia where $R^1 = C_2H_5$).

The compounds of this invention can be administered orally to humans at a dose of from about 250 mg to about 3000 mg per day for an adult which can be given in divided doses, normally in three times a day. The compounds can be administered in a conventional dosage form such as tablet, capsule, powder or syrup which can contain certain conventional binders such as hydroxymethylpropyl cellulose, carboxymethyl cellulose and the like, surface active agents such as polyoxyethylene stearate (MYS-40), excipients (vehicles) such as starch, lactose, glucose and the like which are well known in the art.

Typical pharmaceutical formulations are set forth below, but it is to be understood that the compounds of the present invention can be formulated in other dosage forms which are suitable for oral administration and which are well known in the art.

| Formulation I (Capsule) | |
|---|---|
| Compound Ia (R¹ = C₂H₅) | 250 mg |
| Corn Starch | 37.5 mg |
| Hydroxymethylpropyl Cellulose | 7.5 mg |
| Magnesium Stearate | 2.5 mg |
| Polyoxyethylene Stearate | 2.5 mg |
| Total | 300 mg |

| Formulation II (Capsule) | |
|---|---|
| Compound Ia (R¹ = C₂H₅, Sodium Salt, Monohydrate) | 289.7 mg |
| Corn Starch | 30.3 mg |
| Hydroxymethylpropyl Cellulose | 7.5 mg |
| Magnesium Stearate | 2.5 mg |
| Total | 330 mg |

The above formulation can be filled in a hard gelatin capsule and administered orally.

While the invention has been described in detail and with reference to specific embodiments thereof, it will be apparent to one skilled in the art that various changes and modifications can be made therein without departing from the spirit and scope thereof.

What is claimed is:

1. A compound of the formula (I)

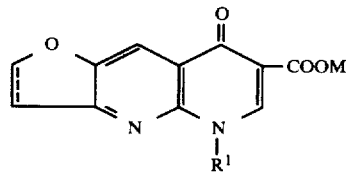

wherein $R^1$ represents an alkyl group having 1 to 6 carbon atoms, and M represents a hydrogen atom, an alkali metal or an alkaline earth metal.

2. The compound of claim 1, wherein said compound of the formula (I) is 5-ethyl-5,8-dihydro-8-oxofuro[3,2−b]-1,8-naphthyridine-7-carboxylic acid.

3. The compound of claim 1, wherein said compound of the formula (I) is sodium 5-ethyl-5,8-dihydro-8-oxofuro[3,2−b]-1,8-naphthyridine-7-carboxylate.

4. The compound of claim 1, wherein said compound of the formula (I) is 5-ethyl-2,3,5,8-tetrahydro-8-oxofuro[3,2−b]-1,8-naphthyridine-7-carboxylic acid.

5. A compound according to claim 1 of the formula (Ia)

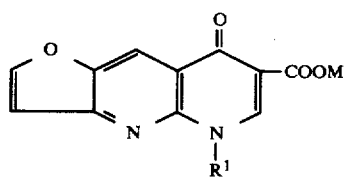

wherein $R^1$ represents an alkyl group having 1 to 6 carbon atoms, and M represents a hydrogen atom, an alkali metal or an alkaline earth metal.

6. A compound according to claim 1 of the formula (Ib)

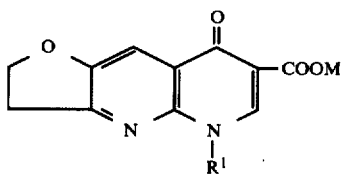

wherein $R^1$ represents an alkyl group having 1 to 6 carbon atoms, and M represents a hydrogen atom, an alkali metal or an alkaline earth metal.

* * * * *